(12) United States Patent
Cammarata

(10) Patent No.: US 8,216,194 B2
(45) Date of Patent: Jul. 10, 2012

(54) HOT FLASH TREATMENT SYSTEM

(76) Inventor: Marie Cammarata, Salem, NH (US)

(*) Notice: Subject to any disclaimer, the term of this patent is extended or adjusted under 35 U.S.C. 154(b) by 1075 days.

(21) Appl. No.: 11/974,111

(22) Filed: Oct. 11, 2007

(65) Prior Publication Data

US 2008/0033376 A1 Feb. 7, 2008

(51) Int. Cl.
*A61M 35/00* (2006.01)
*A01N 65/00* (2009.01)
*A01N 45/00* (2006.01)

(52) U.S. Cl. .............. 604/290; 424/744; 514/170
(58) Field of Classification Search .............. 604/289, 604/290; 424/484, 491, 562, 744, 59, 476, 424/725; 514/170, 171, 173, 177
See application file for complete search history.

(56) References Cited

U.S. PATENT DOCUMENTS

| | | | |
|---|---|---|---|
| 2,915,529 A | 12/1959 | Bell, Jr. | |
| 3,637,774 A | 1/1972 | Babayan et al. | |
| 5,646,190 A * | 7/1997 | Martin | 514/724 |
| 5,721,305 A | 2/1998 | Eshuis et al. | |
| 6,558,710 B1 * | 5/2003 | Godfrey | 424/642 |
| 2003/0003107 A1 * | 1/2003 | Farmer | 424/184.1 |
| 2004/0185088 A1 * | 9/2004 | Pearson et al. | 424/443 |
| 2004/0185115 A1 * | 9/2004 | Pearson et al. | 424/522 |
| 2004/0220087 A1 * | 11/2004 | Bar-Or | 514/7 |

FOREIGN PATENT DOCUMENTS

| | | |
|---|---|---|
| EP | 0739888 | 10/1996 |
| FR | 2778182 | 4/1998 |

OTHER PUBLICATIONS

Cooper A, Spencer C, Whitehead MI, Ross D, Barnard GJR, Collins WP, (1998) Systemic absorption of progesterone from Progest cream in postmenopausal women. Lancet, 351, pp. 1255-1256.*
Ingredient listing for Pro-gest® Cream, Exhibit A of FTC Complaint D-9325 against Herbs Nutrition Corp, (2003) http://www.ftc.gov/os/adjpro/d9325/071005herbscmpltexhibita.pdf, p. 12.*
*Total and Partial Erucate of Pentaerythritol. Infrared Spectrocopy Study of Relationship Between Structure, Reactivity, and Thermal Properties*, JAOCS, vol. 75, No. 2 (1998) pp. 293-299.
*Fatty Acids in Industry, Dibasic Fatty Acids*, Robert W. Johnson, Marcel Dekker, Inc., pp. 327-350.
*Transesterification*, Junzo Otera, Chem. Rev. 1993, 93, 1449-1470.
*Standard Test Method for Kinematic Viscosity of Transparent and Opaque Liquids (and the Calculation of Dynamic Viscosity)*, ASTM International Designation: D 445-04$^{e2}$, pp. 1-10.
*Standard Test Method for Wear Preventive Characteristics of Lubricating Fluid (Four Ball Method)*, ASTM D 4172, Janvier 1994, Designation: D 4172-94, pp. 1-5.
*Standard Test Method for Measurement of Extreme-Pressure Properties of Lubricating Fluids (Four-Ball Method)*, ASTM International Designation: D 2783-03, pp. 1123-1131.
*Standard Test Method for Pour Point of Petroleum Products*, ASTM International Designation: D 97-08, pp. 1-10.
*Standard Test Method for Heat of Combustion of Liquid Hydrocarbon Fuels by Bomb Calorimeter*, ASTM Designation D 240-02, Janvier 2002, pp. 1-9.
Ray et al., *Polycarbonate and Poly(Carbonate-Ester)s Synthesized from Biocompatible Building Blocks of Glycerol and Lactric Acid*, Macromolecules, 36, 3557-3562 (2003).
International Search Report for International Application No. PCT/FR05/003244 dated May 7, 2006.

* cited by examiner

*Primary Examiner* — Melanie Hand
(74) *Attorney, Agent, or Firm* — Eleanor M. Musick; Procopio, Cory, Hargreaves & Savitch LLP

(57) ABSTRACT

A composition comprising an alcohol and an aloe vera gel for topically treating hot flashes and methods for the storing, dispensing and application thereof.

16 Claims, No Drawings

HOT FLASH TREATMENT SYSTEM

CROSS-REFERENCE TO RELATED APPLICATIONS

This application claims priority under 35 U.S.C. 119 of U.S. patent application Ser. No. 11/325,043 filed Jan. 4, 2005 and U.S. provisional application Ser. No. 60/641,231 filed Jan. 4, 2004, the contents of which are fully incorporated herein by reference.

FIELD OF THE INVENTION

The present invention is directed to topical treatments for reducing the symptoms of perimenopausal, menopausal and postmenopausal hot flashes.

BACKGROUND OF THE INVENTION

A hot flash is characterized by a sudden, intense, hot feeling on the face and upper body, perhaps preceded or accompanied by a rapid heartbeat and sweating, nausea, dizziness, anxiety, headache, weakness, or a feeling of suffocation. Some women experience an "aura," an uneasy feeling just before the hot flash, that lets them know what's coming.

The flash is followed by a flush, leaving one reddened and perspiring. The intensity of the flash determines whether the individual becomes soaked in perspiration or merely suffers a moist upper lip. A chill can lead off the episode or be the finale. When hot flashes occur during the night, they can cause sleeplessness (insomnia), resulting in poor concentration, memory problems, irritability and exhaustion during the day.

Researchers do not know exactly what causes hot flashes. Current theories suggest hot flashes are due to a menopause-related drop in the body's level of female hormones called estrogens. This drop affects the hypothalamus, an area of the brain that regulates body temperature. In a hot flash, the hypothalamus seems to sense that the body is too hot even when it is not, and tells the body to release the excess heat. The heart pumps faster, the blood vessels in the skin dilate, particularly those near the skin of the head, face, neck and chest, to circulate more blood to radiate off the heat, and the sweat glands release sweat to cool the body off even more. Once the blood vessels return to normal size, the person feels cool again.

This heat-releasing mechanism is how the body keeps from overheating in the summer, but when a drop in estrogen triggers the process instead, the brain's confused response can make a person very uncomfortable. Some women's skin temperature can rise six degrees Centigrade during a hot flash. The body cools down when it shouldn't, and the person is miserable: soaking wet in the middle of a board meeting or in the middle of a good night's sleep.

Hot flashes affect about 85% of women during the years immediately before and after menopause. Menopause usually occurs around age 51, but hot flashes can begin as early as 2 to 3 years before the last menstrual period. Hot flashes can last for 6 months to as long as 15 years after the final period. The average is two years. Some women have only a few episodes a year, while others have as many as 20 episodes a day.

There is considerable variation in time of onset, duration, frequency, and the nature of hot flashes, whether an individual has had breast cancer or not. An episode can last a few seconds or a few minutes, occasionally even an hour, but it can take another half hour for someone to feel them self again. The most common time of onset is between six and eight in the morning, and between six to ten at night.

Hot flashes occur in women who experience natural menopause, as well as in women who undergo menopause because their ovaries have been removed surgically or because they take medications that lower estrogen levels. These medications include gonadotropin-releasing hormone agonists, such as leuprolide (Lupron) or danazol (Danocrine) that lower estrogen levels. Women that have had breast cancer have hot flashes that can follow the same pattern as for women in general, or they can be more intense and last longer, particularly if menopause was premature, or if you are taking tamoxifen and your body hasn't adjusted to it.

Although hot flashes usually are considered a female problem, men can have hot flashes if their levels of the male sex hormone testosterone drop suddenly and dramatically. For example, hot flashes occur in 75% of men with prostate cancer who have surgery to remove the testes (orchiectomy) or who take medication to decrease testosterone levels.

In addition, symptoms that mimic hot flashes can occur in both men and women who have a tumor of the hypothalamus or pituitary gland, certain serious infections such as tuberculosis or HIV, alcoholism or thyroid disorders. Symptoms that are similar to hot flashes also can be a side effect of the food additive monosodium glutamate (MSG), or of certain medications, particularly nitroglycerin (sold under many brand names), nifedipine (Procardia, Adalat), niacin (numerous brand names), vancomycin (Vancocin) and calcitonin (Calcimar, Cibacalcin, Miacalcin).

Currently, Hormone Replacement Therapy ("HRT"), or the taking of estrogen alone or in combination with progesterone or other hormones, is believed to be one of the most effective treatments available to reduce the onset of hot flashes. These hormones can be taken as a pill, injected, administered through a skin patch and or applied in a cream. For example, for women who have undergone surgical menopause and have unusually severe hot flashes, some studies have shown that a combination of estrogen and androgen may be effective. Alternative medications to help decrease the intensity of hot flashes include clonidine (Catapres), lofexidine (Britlofex), methyldopa (Aldomet), or antidepressants such as venlafaxine (Effexor), paroxetine (Paxil), fluoxetine (Prozac) and sertraline (Zoloft).

In addition to HRT and other medications, several nonprescription dietary supplements or herbal remedies are promoted as natural ways to prevent or treat hot flashes. Several studies in humans suggest that black cohosh, red clover and soy may be safe and effective for improving symptoms of menopause. There are several other known suggested hot flash remedies such as changing one's wardrobe, becoming physically active, reducing intake of triggering foods and beverages and relaxation that are aimed at preventing or reducing the number of hot flashes experienced.

Certain drawbacks exist with current treatments for hot flashes. Because of potential side effects and dangers of hormone therapy, as outlined in several medical studies, many women choose not to use HRT in any form. Also, because other medications or dietary supplements are often ineffective or can cause undesired effects, many women choose to forgo these treatments as well.

Even when effective, however, the above-mentioned remedies are geared at reducing the onset of a hot flash rather than treating the symptoms or relieving the discomfort of an ongoing hot flash. Therefore, when a hot flash occurs, these treatments do little if anything to reduce the intense hot feeling on the face and upper body, rapid heartbeat, sweating, nausea, dizziness, anxiety, headache, weakness or a feeling of suffocation.

Presently there are no known hot flash treatments that include a topical solution for the safe, simple and immediate treatment of hot flash symptoms. Accordingly, a need exists for such a remedy.

SUMMARY OF THE INVENTION

It is therefore an object of the present to provide a non-hormonal and or non-prescription remedy for the safe, simple and immediate treatment of hot flash symptoms The present invention includes a topical solution and or a disposable cloth containing a topical solution for the treatment of perimenopausal, menopausal and postmenopausal hot flash symptoms.

The topical solution is applied to certain parts of the body, which cools the body and relieves the symptoms associated with a hot flash. Reducing the body's temperature or deceiving the body into believing that it is cooler reduces the severity of the hot flash.

Other objects will, in part, be obvious and will, in part, appear hereinafter. The invention accordingly, comprises the features of construction, combination of elements and arrangements of parts, which will be exemplified in the following detailed description and the scope of the invention will be indicated in the claims.

According to one aspect of the invention, a method of alleviating the symptoms of menopausal hot flashes in a human, comprising selecting a subject in need of treatment for hot flashes; and applying an amount of solution to certain parts of the subject's body, wherein the solution effectively cools the subject's body is disclosed.

As to another aspect of the invention, a topical solution for treating the symptoms associated with a hot flash, comprising an alcohol and an aloe vera gel is disclosed.

As to yet another aspect of the invention, a treatment for the symptoms of a hot flash comprising a topical solution; a container for storing and or dispensing said topical solution is disclosed.

DETAILED DESCRIPTION

For purpose of illustration, and not to limit generally, the present invention will now be described with specific reference to certain embodiments. In a first aspect, the invention provides a composition comprising an aloe vera gel and an alcohol. The composition can be formulated to provide quick and sustained release of the active ingredients after administration to a patient by employing procedures known in the art.

In certain embodiments of the present invention the topical solution is non-hormonal and or non-prescription and is applied in liquid, lotion, gel or other equally suitable form. The topical solution may also be applied via a disposable piece of paper or cloth such as a towelette impregnated with the topical solution or in a roll-on form.

To treat the symptoms of a hot flash a user applies the topical solution to their arms, neck and or other parts of their body. In a preferred embodiment, the topical solution is applied to the back of both arms, starting at the wrists, and to the back of the neck. Application of the topical solution to the user's body parts simulates rinsing in cool water, and therefore reduces the heat sensations normally felt during a "hot flash".

The topical solution may be dispensed from a variety of different containers including, but not limited to, bottles, tubes, pop-up wipe plastic tubs, foil or plastic pouches, individual tearable pouches, and the like. In certain embodiments, small individual containers that are appropriate for carrying in a pocket or purse are contemplated.

In a certain embodiment the composition includes one or more of an Aloe Vera Gel, Alcohol, Triethanolamine, Tocopheryl acetate, Carbomer 940, Tetrasodium EDTA, DMDM Hydantoin and Diazolidinyl urea. In certain embodiments the alcohol is an Isopropyl Alcohol.

The composition may include one or more of the following optional additives such as colorants, perfumes, etc. In practice, each of these additives should be both miscible and compatible with the other ingredients of the composition. Compatible additives are those that do not prevent the use of the composition in the manner prescribed herein.

The composition may be administered in a therapeutically effective amount. It will be understood that the amount of the composition actually administered may be determined by the individual in light of the relevant circumstances, including the severity of the condition to be treated, the chosen route of administration, the actual composition administered and the age, weight and response of the individual, and the like.

The composition is applied to the skin surface of the patient at the desired site. The composition may be applied to the face, scalp, neck, trunk, back, limbs, axillae, and/or groin of the individual. Preferably, the composition is applied to the back of each arm beginning at the wrists and to the back of the neck. It has been found that the application of the composition to the skin of humans suffering from hot flashes reduces or eliminates the symptoms thereof.

The compounds of the present invention may be administered in a composition comprising the active compounds in combination with an acceptable carrier adapted for topical administration. Topical compositions may be in the form of a solution, cream, ointment, mousse, gel, lotion, powder or aerosol formulation adapted for application to the skin. These topical compositions containing the compounds of the present invention preferably include from about 50% to 70% by weight aloe vera gel and preferably include from about 20% to 30% by weight an alcohol, although other combinations and percentages of ingredients are contemplated and are believed to perform suitably.

Topical preparation containing the active compound can be admixed with a variety of carrier materials or pharmaceutically acceptable excipients well known in the art. When the excipient serves as a dilutent, it can be a solid, semi-solid, or liquid, which acts as a vehicle, carrier or medium for the active ingredient. Thus, the compositions can be in the form of powders, suspensions, emulsions, solutions, syrups, alcoholic solutions, ointments, topical cleansers, cleansing creams, skin gels, skin lotions, mousses, roll-ons, aerosol or non-aerosol sprays in cream or gel formulations and soft gelatin capsules.

Having thus described multiple illustrative embodiments of the invention, various alterations, modifications and improvements will readily occur to those skilled in the art. Such alterations, modifications and improvements are intended to be within the scope and spirit of the invention. Accordingly, the foregoing description is by way of example only and is not intended as limiting. The invention's limit is defined only in the following claims and the equivalents thereto.

What is claimed is:

1. A method of alleviating the symptoms of menopausal hot flashes in a human, comprising: a. selecting a subject in need of treatment for hot flashes; and b. applying an amount of solution comprising an alcohol and an aloe vera gel to certain parts of the subject's body, wherein the solution comprises from about 20% to about 30% by weight of an isopropyl alcohol and from about 50% to about 70% by weight of an aloe vera gel; wherein the solution effectively cools the subject's body.

2. The method of claim 1 wherein the solution is applied to the back of the subject's neck and arms.

3. The method of claim 1 wherein the solution is in the form of a lotion.

4. The method of claim 1 wherein the solution is in the form of a gel.

5. The method of claim 1 wherein the solution is in the form of a roll-on.

6. The method of claim 1 wherein the solution is in the form of a cream.

7. The method of claim 1 wherein the solution is in the form of a towelette impregnated with a lotion.

8. A topical solution for treating the symptoms associated with a hot flash, comprising from about 20% to about 30% by weight of an isopropyl alcohol and from about 50% to about 70% by weight of an aloe vera gel.

9. The topical solution of claim 8 wherein the topical solution further includes one or more of the group of ingredients comprising Triethanolamine, Carbomer 940, DMDH Hydanton, Diazolidinyl, Tetra-sodium EDTA and Tocopheryl Acetate.

10. The topical solution of claim 8 further comprising a fragrance.

11. The topical solution of claim 8, wherein the solution is in the form of a lotion.

12. The topical solution of claim 8, wherein the solution is in the form of a gel.

13. The topical solution of claim 8, wherein the solution is in the form of a roll-on.

14. The topical solution of claim 8, wherein the solution is in the form of a cream.

15. The topical solution of claim 8, in the form of a towelette impregnated with the solution.

16. A composition for alleviating symptoms associated with a hot flash, comprising from about 50% to about 70% by weight of an aloe vera gel and from about 20% to about 30% by weight of an isopropyl alcohol; wherein the composition is adapted for topical application to the skin of an individual experiencing hot flash symptoms in an amount sufficient to induce alleviation of the symptoms.

* * * * *